United States Patent [19]
Ishikawa

[11] 3,932,133
[45] Jan. 13, 1976

[54] SYSTEM FOR DETECTING THE PARTICULAR CHEMICAL COMPONENT OF A TEST FLUID

[75] Inventor: Hiroshi Ishikawa, Fussa, Japan

[73] Assignee: Olympus Optical Co., Ltd., Tokyo, Japan

[22] Filed: July 23, 1974

[21] Appl. No.: 491,110

[30] Foreign Application Priority Data

| July 31, 1973 | Japan | 48-86167 |
| July 31, 1973 | Japan | 48-86170 |
| July 31, 1973 | Japan | 48-86173 |
| Dec. 12, 1973 | Japan | 48-142126 |
| June 20, 1974 | Japan | 49-72343 |

[52] U.S. Cl......... 23/253 R; 23/253 TP; 235/151.35
[51] Int. Cl.²................. G01N 33/16; G01N 21/30
[58] Field of Search......... 23/253 R, 253 TP, 259, 23/230 R; 235/151.35

[56] References Cited
UNITED STATES PATENTS

| 3,368,872 | 2/1968 | Natelson | 23/253 R |
| 3,497,320 | 2/1970 | Blackburn | 23/253 R |
| 3,526,480 | 9/1970 | Findl et al. | 23/253 TP |
| 3,554,700 | 1/1971 | Maxon | 23/253 R |
| 3,607,090 | 9/1971 | Maxon | 23/253 TP |
| 3,620,678 | 11/1971 | Guigan et al. | 23/253 R |
| 3,676,080 | 7/1972 | Richterich | 23/259 X |
| 3,728,080 | 4/1973 | Moran | 23/253 R |
| 3,770,382 | 11/1973 | Carter et al. | 23/253 R |

Primary Examiner—R. E. Serwin
Attorney, Agent, or Firm—Flynn & Frishauf

[57] ABSTRACT

A chemical reaction test piece having arranged at prescribed intervals on its elongate substrate a plurality of carriers having impregnated therein reagents and test fluids is mounted on a table, and the reflection light of a light irradiated onto the carrier from a lamp is converted into a measurement electrical signal by a photoelectric converter. A reference reflection carrier is further provided on said substrate or table, and a light reflected from said reference reflection carrier is converted into a reference electrical signal by the photoelectric converter, and said measurement electrical signal is calibrated relative to a change with time in a signal detection system including said lamp and photoelectric converter using said reference electrical signal. The calibrated measurement electrical signal is subjected to data processing to be converted into a test data, and this test data is compared with a reaction comparison data previously stored in a memory, and the comparison result is printed on a recording paper by a printer.

9 Claims, 25 Drawing Figures

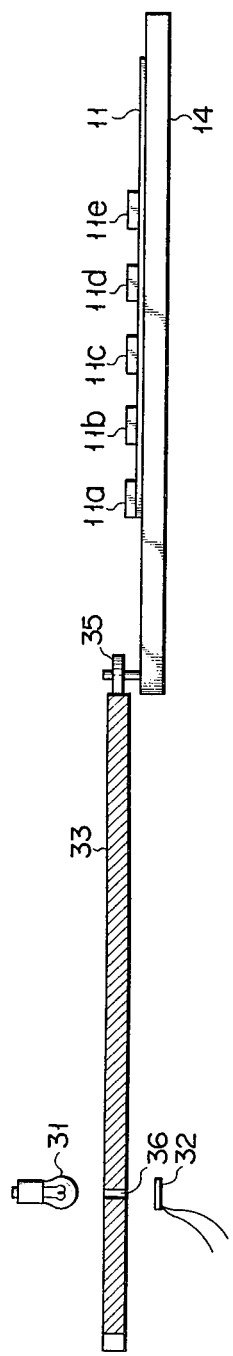
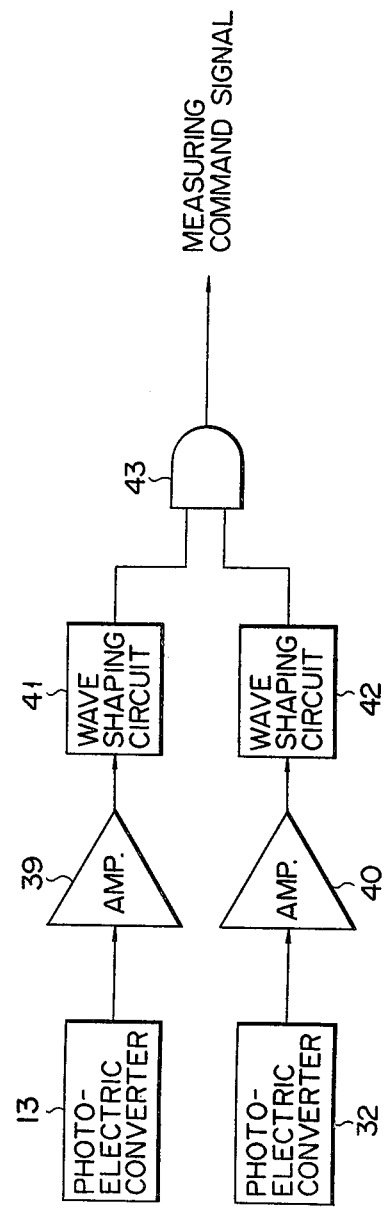

FIG. 10

| NUMBER OF REAGENT | CODE | | | | | | | |
|---|---|---|---|---|---|---|---|---|
| | t1 | t2 | t3 | t4 | t5 | t6 | t7 | t8 |
| ONE | O | O | O | O | O | O | ⊖ | — |
| | O | O | O | O | O | ⊖ | O | — |
| | O | O | O | O | ⊖ | O | O | — |
| | O | O | O | ⊖ | O | O | O | — |
| | O | O | ⊖ | O | O | O | O | — |
| | O | ⊖ | O | O | O | O | O | — |
| | ⊖ | O | O | O | O | O | O | — |
| TWO | O | O | O | O | O | ⊖ | — | — |
| | O | O | O | O | ⊖ | O | — | — |
| | O | O | O | ⊖ | O | O | — | — |
| | O | O | ⊖ | O | O | O | — | — |
| | O | ⊖ | O | O | O | O | — | — |
| | ⊖ | O | O | O | O | O | — | — |
| THREE | O | O | O | O | ⊖ | — | — | — |
| | O | O | O | ⊖ | O | — | — | — |
| | O | O | ⊖ | O | O | — | — | — |
| | O | ⊖ | O | O | O | — | — | — |
| | ⊖ | O | O | O | O | — | — | — |
| FOUR | O | O | O | ⊖ | — | — | — | — |
| | O | O | ⊖ | O | — | — | — | — |
| | O | ⊖ | O | O | — | — | — | — |
| | ⊖ | O | O | O | — | — | — | — |
| FIVE | O | O | ⊖ | — | — | — | — | — |
| | O | ⊖ | O | — | — | — | — | — |
| | ⊖ | O | O | — | — | — | — | — |
| SIX | O | ⊖ | — | — | — | — | — | — |
| | ⊖ | O | — | — | — | — | — | — |
| SEVEN | ⊖ | — | — | — | — | — | — | — |

FIG. 9

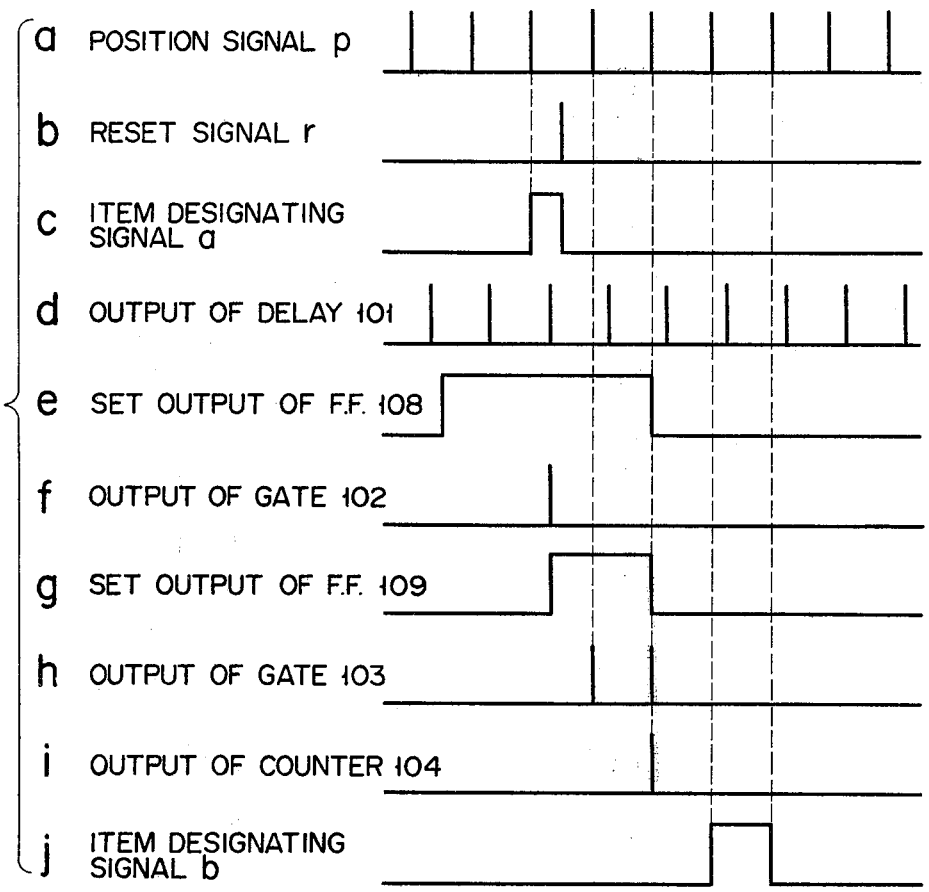

SYSTEM FOR DETECTING THE PARTICULAR CHEMICAL COMPONENT OF A TEST FLUID

BACKGROUND OF THE INVENTION

This invention relates to a system for detecting the particular chemical component of a test fluid, for obtaining an electrical signal for detecting the particular chemical component of the test fluid in accordance with a change in the color of a carrier, i.e., reagent effected due to the chemical reaction of a reagent impregnated or contained in the carrier on a chemical reaction test piece with a test fluid added to said carrier.

Conventionally, as shown in FIG. 1, a chemical reaction test piece 11 is known which has arranged on at prescribed intervals and adhered onto its elongate transparent substrate 10 a plurality of carriers 11a, 11b, 11c and 11d having coated thereon or impregnated therein different types of chemical reaction reagents. Said test piece is generally used for test of a test fluid, e.g., the urine. The usual method for testing a test fluid using said test piece comprises immersing the test piece in the test fluid or dropping the test fluid onto a reagent carrier to impregnate said test fluid in said test piece, subjecting the test fluid and reagent to a chemical reaction for a prescribed length of time, comparing the color of the reagent, i.e., reagent carrier changing in accordance with the degree of said chemical reaction with the colors of a color comparison table thereby to investigate what reaction degree said color indicates, in other words, the sequential position of said reaction degree, thus to determine the nature, for example, concentration, pH and the like of the test fluid.

Accordingly, since the usual test using the foregoing chemical reaction test piece is carried out by artificially comparing the color of a reagent carrier with that of a color comparison table, such test is troublesome, inefficient and inaccurate, and also insanitary because, for example, in the urine test, the urine is directly manually handled.

SUMMARY OF THE INVENTION

This invention is intended to provide a system for detecting the particular chemical component of a test fluid which is adapted to enable an efficient and accurate test to be performed sanitarily, and this object can be attained by constructing a system for detecting the particular chemical component of a test fluid wherein a chemical reaction test piece having those carriers containing reagents to which a test fluid is added is mounted on a table; and a detector including a light source and a photoelectric converter is moved relative to the chemical reaction test piece thereby obtaining an electrical signal indicating the degree of the reaction of the reagent with the test fluid from the photoelectric converter, thus carrying out the test of the test fluid.

BRIEF DESCRIPTION OF THE DRAWINGS

FIG. 7 is a longitudinal sectional view of the device shown in FIG. 6;

FIG. 8 is a block circuit diagram illustrating a position signal detector for detecting the position signals of carriers on the chemical reaction test piece;

FIG. 9 shows examples of the chemical reaction test piece used in the testing system of the invention;

FIG. 10 shows the relationship between the number of reagents in the test piece and codes indicating said reagents;

FIG. 22 shows signal waveforms showing the operation timing of respective sections of FIG. 21;

FIG. 24 is a view for explaining the content of test data supplied to the device illustrated in FIG. 23; and FIG. 25 shows the relationship between the characters of the printing drum and the respective corresponding contents of the counters of FIG. 23.

DESCRIPTION OF PREFERRED EMBODIMENTS

Figure 1:
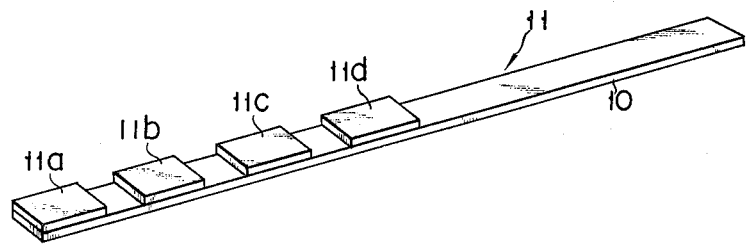
FIG. 1 is a perspective view illustrating a chemical reaction test piece used for the test of the particular chemical component of a test fluid.
Figure 2:
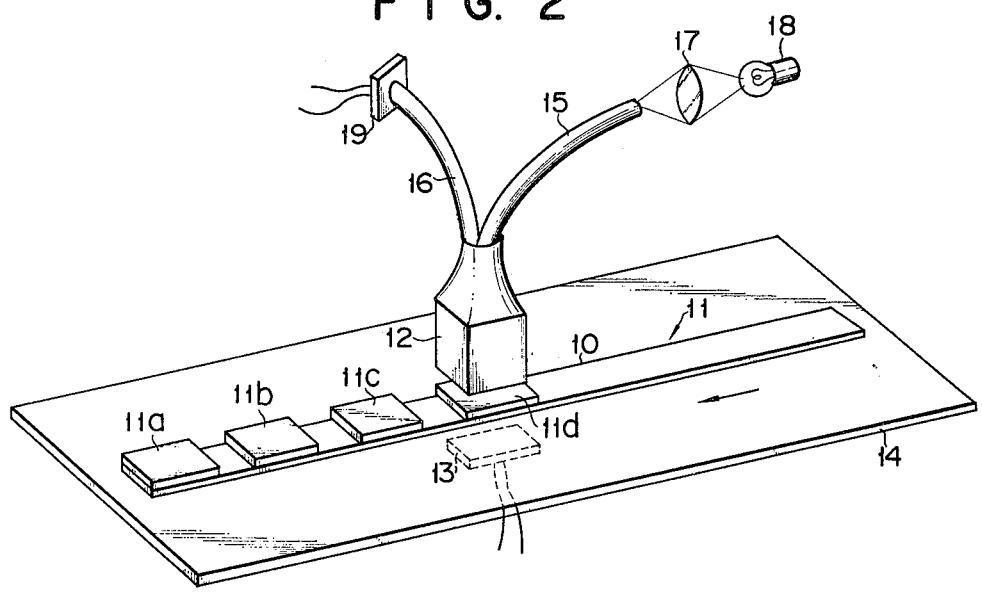
FIG. 2 is a perspective view illustrating aa photoelectric detector in a testing system according to the invention.

Referring to FIG. 2, a light transmitting and receiving means 12 and a photoelectric conversion element 13 are arranged in a manner facing each other at a prescribed interval. Between the light transmitting and receiving means 12 and the photoelectric conversion element a chemical reaction test piece 11 is mounted on a transparent table 14 so as to cause reagent carriers 11a to 11d to oppose the light transmitting and receiving means 12, and, when the transparent table 14 is intermittently moved by a table driving device as later described, one of the reagent carriers 11a to 11d is stopped in turn between the light transmitting and receiving means 12 and photoelectric conversion element 13. Two light guides 15 and 16 are connected at one end to the light transmitting and receiving means 12. A lamp 18 is connected to the other end of the light guide 15 via a lens 17, and a test data detecting-photoelectric conversion element 19 is connected to the other end of the light guide 16. The photoelectric conversion element 13 is provided for the purpose of detecting the type of the test piece 11 and is intended to draw out a signal indicating a code formed correspondingly to the arrangement of the carriers 11a to 11d of the test piece 11 and portions of the transparent substrate 10 between the carriers. For instance, suppose that the table 14 is moved in an arrow-indicated direction to cause the carrier 11d to be brought to the shown position, then a light from the lamp 18 will intermittently be shut off by the carriers 11a, 11b, 11c and 11d. Further, when one of said substrate portions is brought below the means 12, said light passes therethrough to reach the element 13. As the result, the output of the element 13 becomes a signal indicating a code of (0101010). This code represents the carrier 11d of the test piece 11. Further, the photoelectric conversion element 19 produces an electrical signal corresponding to a light reflected from, for example, the carrier 11d. Since this reflected light bears a color corresponding to the chemical reaction of a reagent contained in the carrier 11d with a test fluid added thereto, said electrical signal has an amplitude corresponding to the degree of said chemical reaction. Thus, an analog signal obtained from the photoelectric converter 19 is converted into a digital signal by an analogdigital converter 20, and processing of data calibration, unifying of data size and so on are effected by an operation circuit 21 to obtain a reaction measurement data, which is then input to a comparator 22.

A detection signal obtained from a type detector 23 is converted into a type detection data by a gate circuit 24.

On the other hand, a memory 25 is provided in which there are previously stored reaction comparison data for determining the sequential positions of the respective reaction degrees of various reagent carriers. Said type detection data is the one for sequentially reading out, in accordance with the measurement order of the reagent carriers on the test piece 11, the reaction comparison data corresponding to said reagent carriers, from said memory 25, and is intended sequentially to designate the type of reagents.

The reaction comparison data sequentially read out from the memory 25 by said type detection data is supplied to the comparator 22.

The comparator 22 compares the reaction measurement data with the reaction comparison data, thereby forming rank data obtained by determining the sequential positions of said reaction measurement data, i.e., data presenting the reaction degrees of test reagent carriers, said rank data being input to a printer 26 as an output device. Further, this printer 26 is supplied with said type detection data, and causes both the rank data and the type detection data to be combined selectively to operate the printing mechanism, thereby printing test results obtained by determining the sequential positions of the respective reagent carriers, on a test paper. For example, where the reagent carrier 11d is the one used for the pH test of the urine, printing characters "5", "6", "7", "8" and "9" are selected by the type detection data and, for example, the character "5" is selected from said printing characters by the rank data, whereby the test result of "pH 5" is printed on the test paper.

Figure 4:
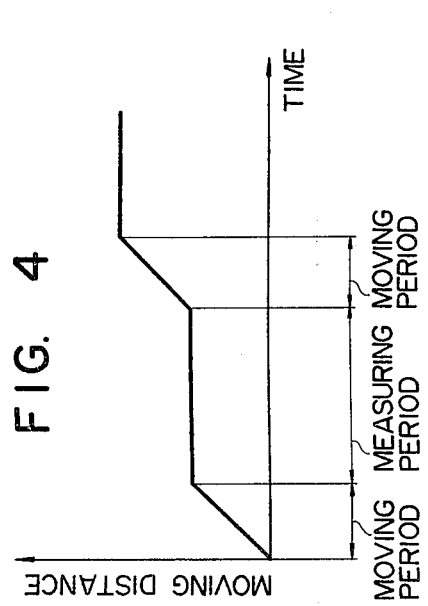
FIG. 4 graphically shows the manner in which the chemical reaction test piece in the photoelectric converter shown in FIG. 2 is intermittently moved during testing.

It is preferred that said chemical reaction test piece 11, as shown in FIG. 4, is intermittently moved and that measurement is not carried out during said movement but during the stoppage of the test piece 11. In this case, accordingly, it is necessary to detect the position of the test piece 11 or the position of the table 14 and commence such measurement in accordance with the detected position signal. In the case shown in FIG. 2, position detection is made utilizing a charge in the output level of the photoelectric element 13 disposed below the table 14, namely, a reduction in said output level more attained when, for example, the reagent carrier 11d is positioned above the element 13 than when the transparent substrate 10 is positioned above the element 13. In this case, a position signal is generated at the edge portion of the reagent carrier. However, since, at this time, the photoelectric element 19 is still situated in a position facing the end portion of said reagent carrier, the commencing of measurement under this condition renders a measurement error large.

Figure 5:
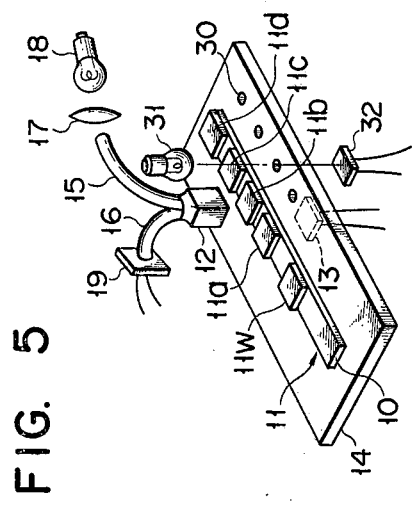
FIG. 5 is a perspective view illustrating an example of the method of detecting a position signal for controlling the intermittent movement of the chemical reaction test piece.

As shown in FIG. 5, apertures 30 may be formed in the table 14 in a manner corresponding to the respective carriers 11a to 11d on the test piece 11, and a lamp 31 and a photoelectric conversion element 32 are respectively provided above and below the table 14 with the aperture 30 corresponding to the measurement position of the test piece 11 interposed therebetween, whereby a position signal is drawn out from said element 32.

Figure 6:
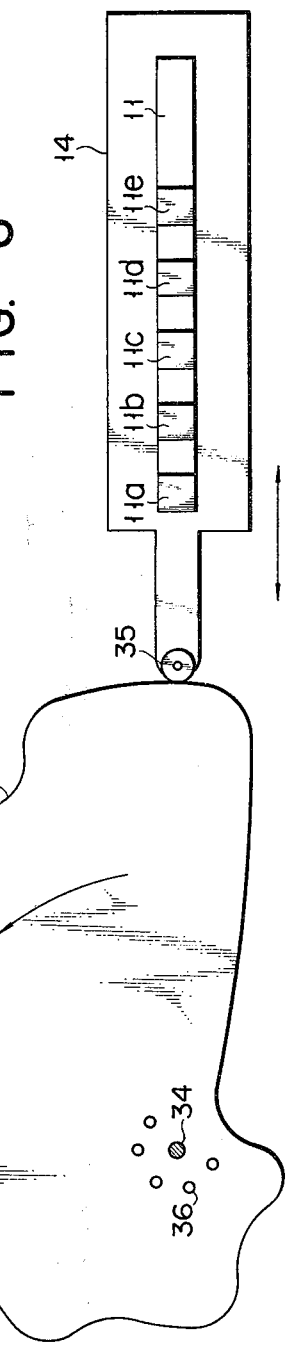
FIG. 6 is a plan view illustrating a device for intermittently moving the chemical reaction test piece.
Figure 11:
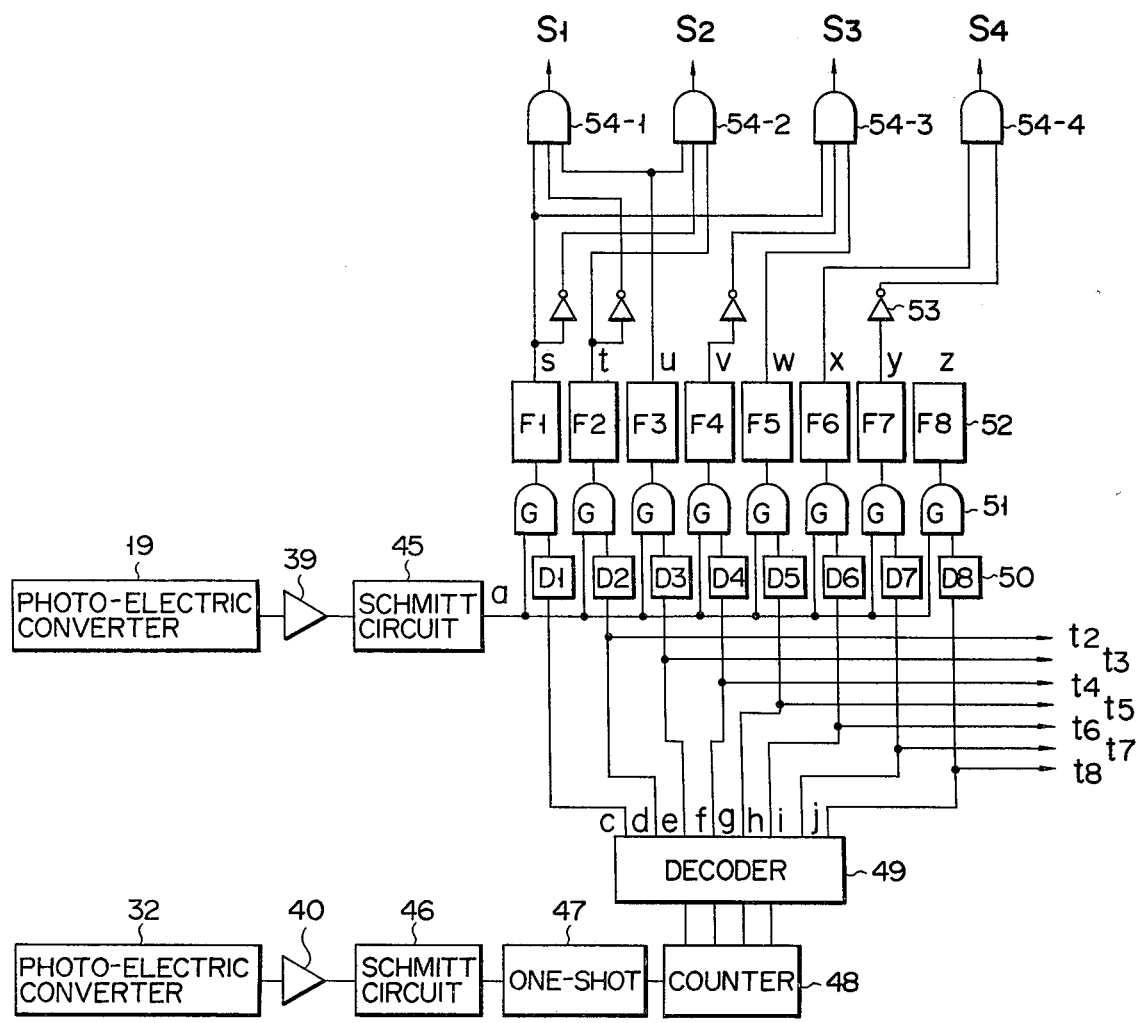
FIG. 11 is a block circuit diagram illustrating a circuit for judging the type of the reagents using the codes of FIG. 10.

FIGS. 6 and 7 show a device capable of generating a position signal under the condition in which the table 14 is stopped with the element 13 and the head section of the element 19 arranged exactly to oppose the central portion of the reagent carrier. Provided is a stepped cam 33 rotating about a shaft 34 with a predetermined speed. Further, a test table 14 is provided approachably to or withdrawably from said cam. By a spring (not shown) a biasing force toward the cam is imparted to said test table 14 thereby causing a roller 35 provided for the tip end portion of the test table 14 to elastically abut agaisnt the cam plane of said cam 33. A plurality of position indication apertures 36 are formed in the periphery of the shaft 34 of the cam 33 at intervals with which the reagent carriers are adhered or attached to the test piece 11 mounted on said test table 14, that is, at intervals respectively corresponding to a pitch at which the test table 14 approaches to or withdraws from the cam 33, and the lamp 31 and the element 32 are provided with said aperture 36 interposed therebetween. The photoelectric conversion element 19 for detecting the reagent carriers on the test piece 11 is provided above said test table 14 as shown in FIG. 2, though not illustrated. A reagent carrier detection signal obtained from the first photoelectric conversion element 19 and an aperture detection signal obtained from the second photoelectric conversion element 32 are respectively amplified by amplifiers 39 and 40, and are respectively subjected to wave-shaping by wave shaping circuits 41 and 42, and thereafter are supplied to an AND circuit 43, and a logical product output of both signals obtained from said circuit 43 is used as a position detection signal or measurement start command signal. If circuit arrangement is made as such, the reagent carrier detection signal will be obtained from the first element 19 when the test table 14 is intermittently moved with the rotation of the cam 33, and the aperture detection signal will be obtained from the second element 32 in a small length of time after said test table 14 has been moved, namely, when the head section 12 of the element 19 of FIG. 2 has been positioned exactly to face the central portion of, for example, the reagent carrier 11d.

Since a logical product output of said both signals is used as the position detection signal, this position detection signal can be generated when the element 19 has been positioned exactly to face the central portion of the reagent carrier, and if measurement is commenced by this signal, a precise measurement will be carried out. Further, since the test table 14 is moved by the stepped cam 33 approachably to or withdrawably from the same, it is possible to keep the cam rotated even under the condition in which the test table 14 is stopped. As the result, a reliable generation of said aperture detection signal is enabled.

In the preceding embodiment, said position detection signal was used as a measurement start command signal, but may of course be used as a signal playing other roles.

There will now be described in detail the code detector provided for judging the type of reagent carriers on the test piece, shown in FIG. 3. Used for this code detection are test pieces each having such a coded carrier arrangement as shown, for example, in FIG. 9. Referring to FIG. 9, a test piece 11-1 has six reagent carriers 11a to 11f corresponding to attachment positions t3 to t8, and further a light-impermeable pad 11w is additionally attached onto the test piece correspondingly to an attachment position t1. Similarly, the pads 11w and prescribed reagent carriers are attached onto test pieces 11-2, 11-3 and 11-4 correspondingly to prescribed attachment positions. If light-impermeable sections having said reagent carriers and pads attached correspondingly to the attachment positions t1, t2, ... t8 are now expressed as "1" and the remaining light-permeable sections having no reagent carrier or pad are expressed as "0", the test pieces 11-1, 11-2, 11-3 and 11-4 different in type, shown in FIG. 9 will be able to be expressed in terms of their type by codes. For example, the test piece 11-1 is expressed by a code of 10111111 and the test piece 11-2 is expressed by a code of 01111111. As the result, said both test pieces can easily be distinguished from each other even if the number of reagent carriers on one test piece is identical to the number of reagent carriers on the other. Particularly, if, as later described, scanning is carried out by the photoelectric conversion element, a detection signal obtained by such scanning will directly become a specified coded signal denoting the type of the scanned test piece, so that the foregoing test pieces are desirable as a test piece for use in an automatic testing apparatus.

If, in case, as shown in FIG. 10, coding of test pieces is effected using the pad 11w as previously described, eight pad or reagent carrier attachment positions t1, t2, ... t8 are provided, 28 types of test pieces in all will be able to be distinguished from each other. This number is sufficient in practice. A circle-enclosed digit 1 of FIG. 10 is a type judgment mark.

There will now be described a type judgement device for judging the type of chemical reaction test pieces. As shown in FIG. 5, in this device, the test table 14 is provided which is lengthwise moved and on which said test piece is mounted. Above the test piece 11 the light projection and reception head 12 of the first photoelectric conversion element 19 is arranged to face, for example, the reagent carrier 11b. The apertures 30 are formed in the test table 14 correspondingly and adjacently to the respective attachment positions t1, t2, ... . t8 of the pad 11w and reagent carriers on the test piece 11 mounted on said test table. The light source 31 and photoelectric conversion element 32 are disposed with the aperture 30 interposed therebetween.

Figure 13:
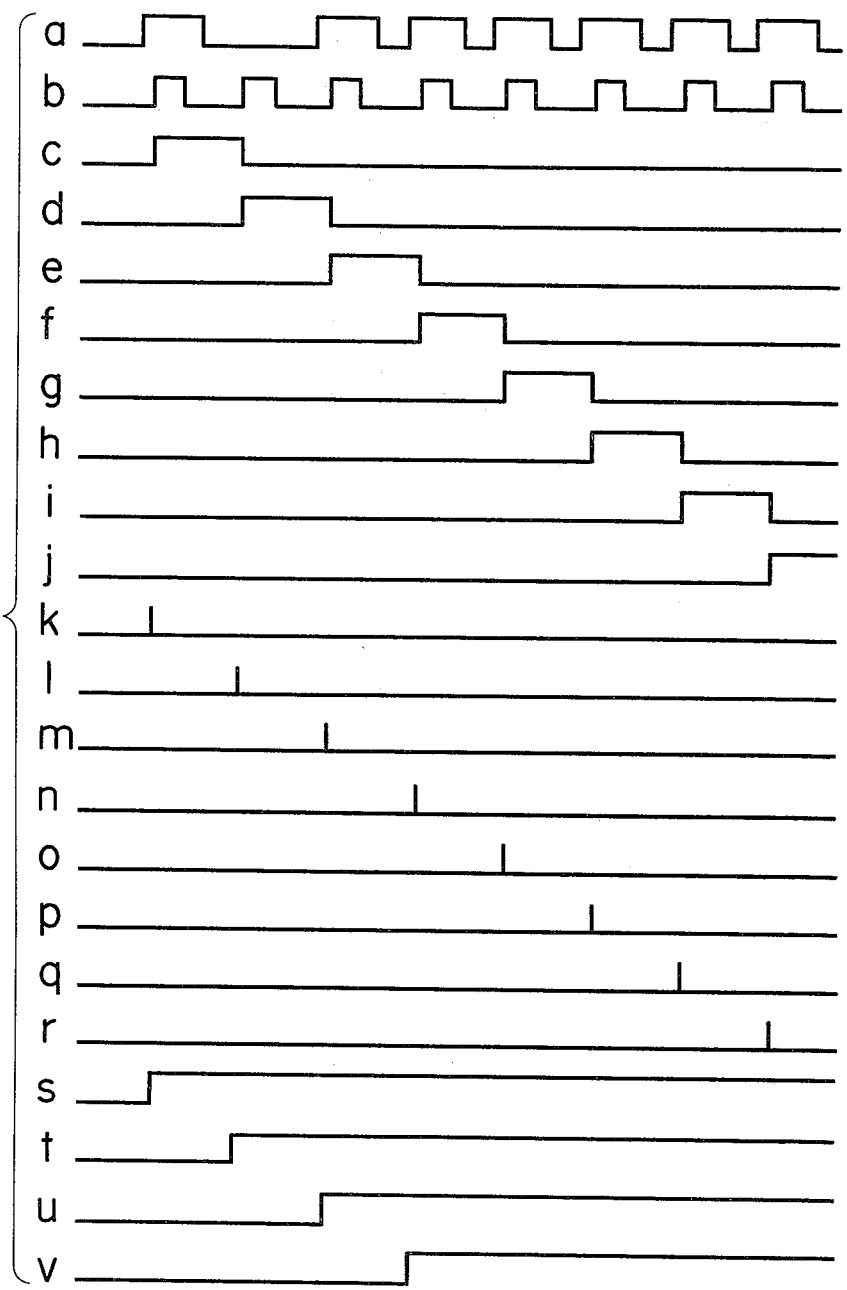
FIG. 13 shows signal waveforms showing the operation of the circuit shown in FIG. 11.

Said transparent test table 14 is formed with a slit in the test piece-mounted section thereof for the purpose of preventing a light from being reflected from those portions of the substrate 10 of the test piece 11 onto which the pads or reagent carriers are not attached, so as to cause a light to pass through said slit, though said slit is not shown. If arrangement is made as such, movement of the test table 14 will cause the first element 19 to scan the test piece 11 and the second element 32 to scan the aperture 30. Therefore, such a coded signal designating a test piece as shown by a of FIG. 13 is obtained from the first element 19 via an amplifier 39 and Schmitt circuit 45. Further, such an aperture detection signal as shown by b of FIG. 13, in other words, the measurement position indication signal of the second element 32 is obtained from the second element 32 via an amplifier 40 and a Schmitt circuit 46.

Accordingly, if arrangement is made such that said measurement position indication signal is counted by a counter 48 via a one-shot circuit 47, the counted output is decoded by a decoder 49, from which is obtained such step-advancement signals as shown by c to j of FIG. 13; these signals are respectively differentiated by a differential circuit 50 and thereby converted into differential signals as shown by k to r of FIG. 13, which are respectively supplied to AND gates 51; and simultaneously said coded signal is supplied to flip-flops F1 to F8 constituting a temporary memory device 52 via a parallel circuit of said AND gates 51, said coded signal will be supplied to the flip-flop correspondingly to said measurement position indication signal.

Accordingly, if the coded signal has, for example, a code of 10111111, the stored content of the flip-flops F1 to F8, i.e., temporary memory device 52 will also have a code of 10111111.

If outputs from the temporary memory device 52, namely, outputs shown by s to z of FIG. 13 are passed through a judgement-logical gate circuit constituted by an inverter group 53 and a group of AND gates 54-1, 54-2, 54-3 and 54-4, type judgement signals S1, S2, S3 and S4 will be obtained from the AND gates 54-1 to 54-4, respectively. The type judgement signals S1, S2, S3 and S4 of said judgement-logical gate circuit are made to correspond to the above-mentioned test pieces 11-1, 11-2, 11-3 and 11-4 of FIG. 9, respectively.

Figure 12:
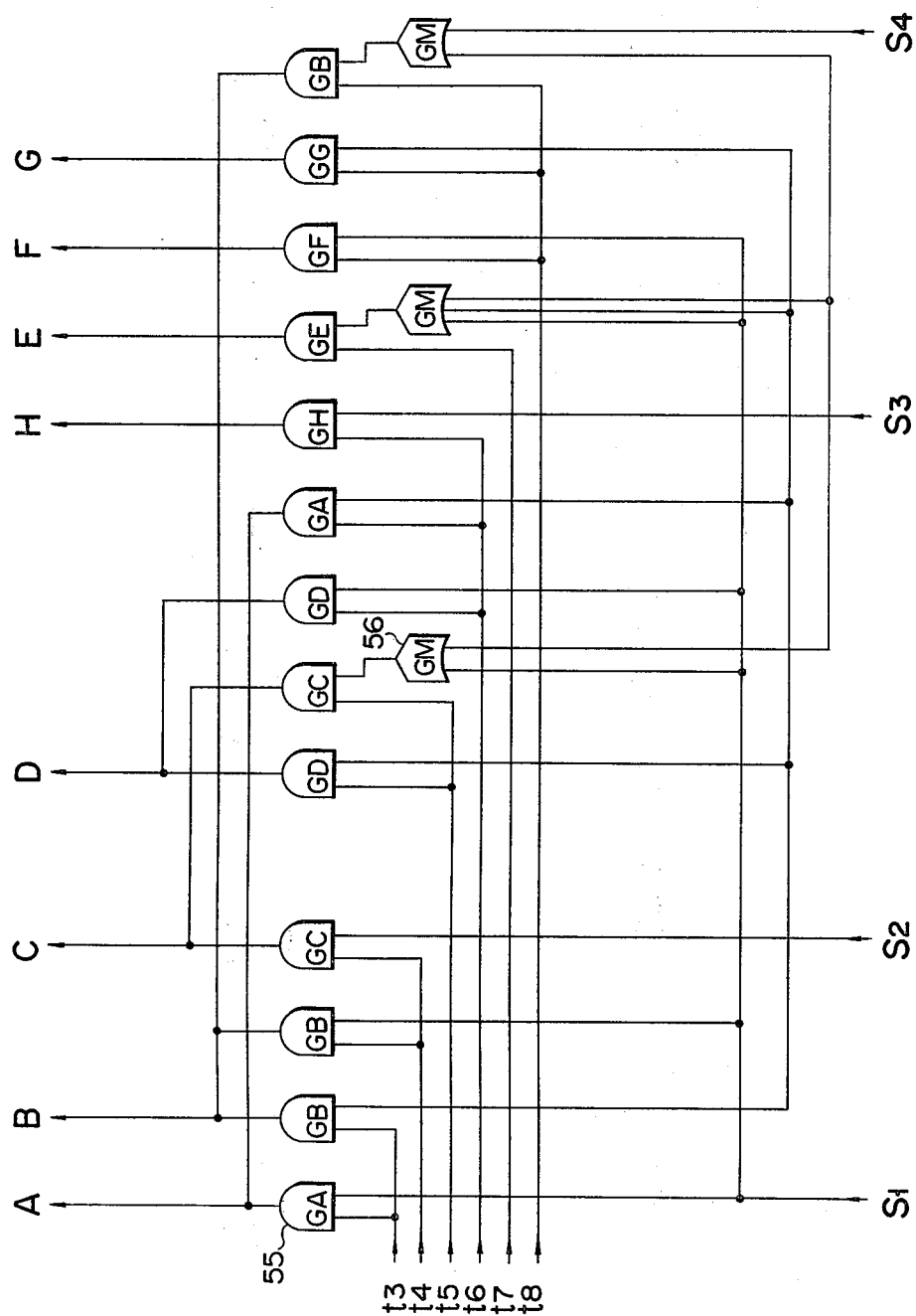
FIG. 12 is a block diagram illustrating a circuit for judging the type of reagent carriers.

If arrangement is made such that, as shown in FIG. 12, the type judgement signals S1, S2, S3 and S4 obtained as above and the step advancement signals t2, t3 ... t8 obtained from said decoder 49, corresponding to the attachment positions t1 to t8 shown in FIG. 9 are ANDed by a judgement-logical product gate circuit consisting of AND gates 55 and OR gates 56, type distinguishment signals A, B, C, D, E, F, G and H representing the reagent carriers 11a to 11h, respectively, will be obtained.

In the case of, for example, a urine test, there are about 15 types of test items and yet the reactions of the urine with the respective reagents require different lengths of time. For this reason, where the cam shown in, for example, FIG. 6 is used, it is difficult to match in timing said reaction time with the rotation speed of the cam 33, that is, the moving speed of the test piece 11.

Figure 14:
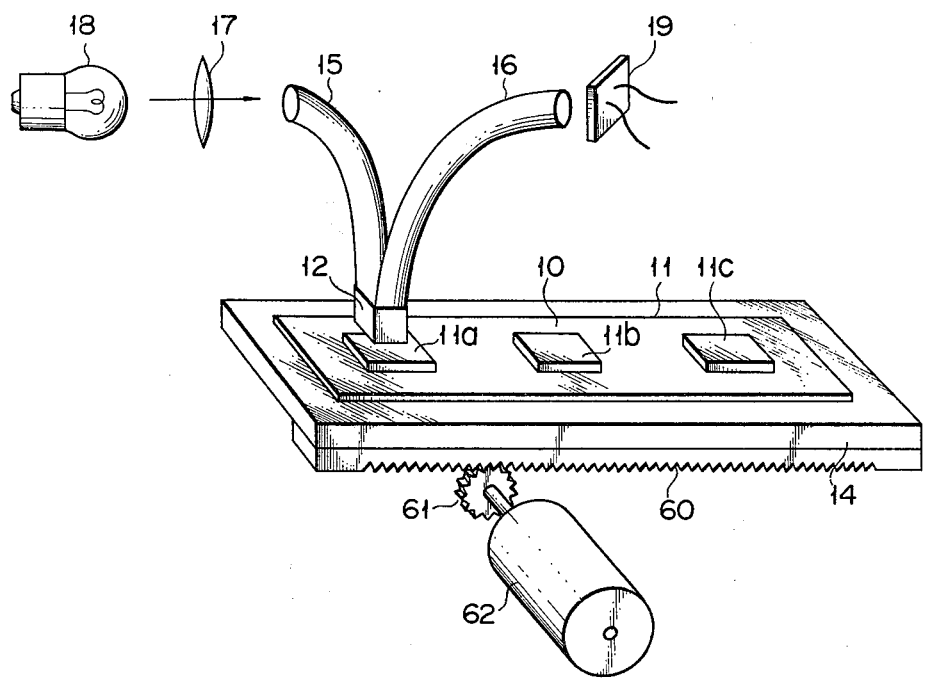
FIG. 14 is a perspective view illustrating an example of a test table for use in the testing system of the invention.

An example of a photoelectric detector improved in the above-mentioned respect is shown in FIG. 14. Referring to FIG. 14, the chemical reaction test piece 11 having the reagent carriers 11a, 11b and 11c is mounted on the table 14. These carriers 11a to 11c respectively contain a reagent for detecting, for example, the pH value, protein component or sugar component in the urine, and are disposed at prescribed intervals respectively defined utilizing the differences in the length of time required for reaction of the urine with the respective reagents and in association with a later described transferring mechanism. On the underside of the test table 14 a rack 60 is provided along the direction in which the table 14 is moved, and the table 14 is moved by rotating a pinion 61 intermeshed with the rack 60 through driving the motor 62.

Figure 15:
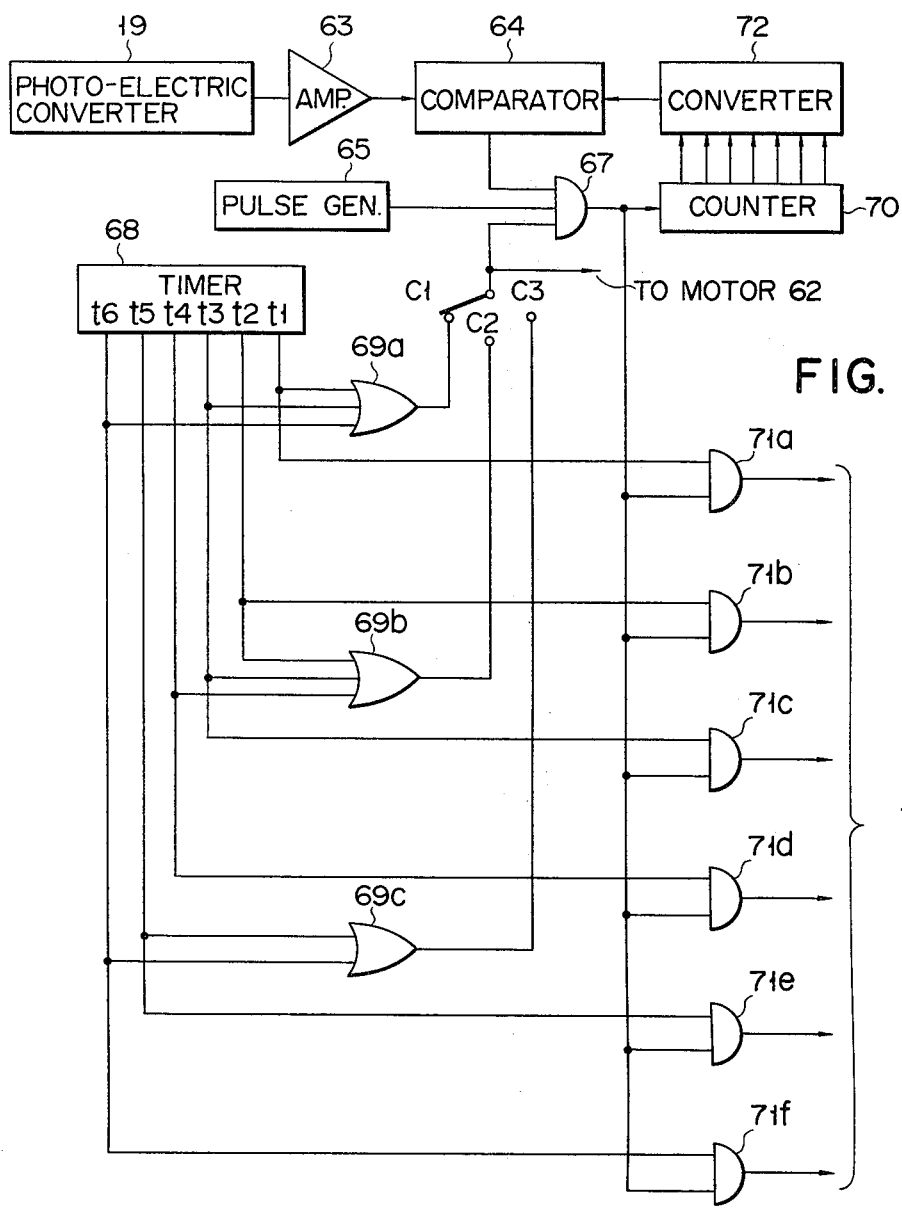
FIG. 15 is a block circuit diagram illustrating a control circuit for controlling the operation of the testing mechanism of FIG. 14.

An electrical signal from the photoelectric conversion element 19 is amplified by an amplifier 63 of FIG. 15 and then is supplied to one input terminal of a comparator 64. The output of the comparator 64 is supplied to the input terminal of an AND gate 67 together with the respective outputs of a pulse oscillator 65 and switch 66. A signal for a timer 68 is supplied to the AND gate 67 via an OR gate 69a and the contact C1 of the switch 66. The output of the AND gate 67 is supplied to a pulse counter 70 and a plurality of judgement AND gate circuits 71a to 71f disposed correspondingly to the lengths of the respective reaction times of the reagents. The outputs of the pulse counter 70 are converted into an analog signal by a digital-analog converter 72 and then said analog signal is supplied to the other input terminal of the comparator 64.

The timer 68 is so formed as to generate those signals of test items correspoonding to reagents, for each length of reaction times designated in accordance with the test items, for example, for each length of times 0 . . . 6, 8, 10, 13 . . . and 60 seconds.

Signals from said timer 68 are supplied to a plurality of OR gate circuits 69a, 69b and 69c corresponding to the reagent carriers 11a, 11b and 11c, respectively, on the test piece 11.

Outputs from the OR circuits 69a, 69b and 69c are supplied to said AND circuit 67 via the contacts C1, C2 and C3, respectively, of the change-over switch 66 and simultaneously are supplied to the drive control circuit (not shown) of said motor 62.

Figure 3:
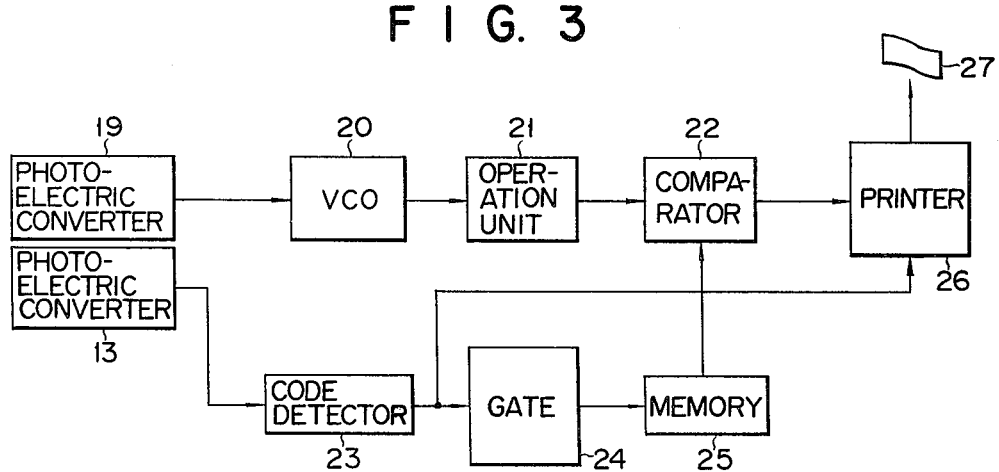
FIG. 3 is a block circuit diagram illustrating a testing system according to an embodiment of the invention.

Outputs from the timer 68 are supplied to the AND gate circuits 71a, 71b, 71c . . . 71f provided in accordance with the respective lengths of reaction times, and outputs from these AND gate circuits 71a to 71f are supplied to the operation circuit 21 of FIG. 3 so as to detect the respective reaction conditions of the reagent carriers.

The photoelectric measurement means of the automatic analysis device having the foregoing construction draws off the test piece 11 immersed in, for example, the test urine, and intermittently feeds the test piece 11 by means of the transferring mechanism, and detects the respective reaction conditions of the reagent carriers 11a, 11b and 11c in turn.

The reaction condition of the carrier 11a is detected by the photoelectric detector 19, and the resulting detection signal is amplified by the amplifier 63 and then supplied to the comparator 64 the output (shown by a of FIG. 16) of which is supplied to the AND circuit 67.

Figure 16:
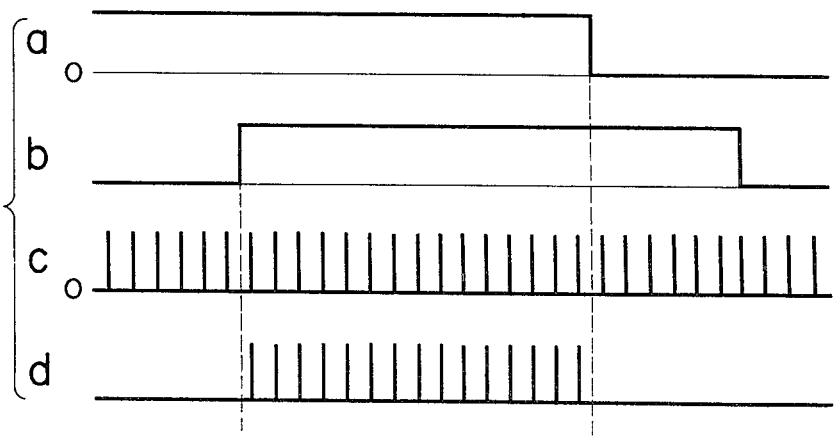
FIG. 16 shows waveforms of signals of FIG. 15.

A pulse signal (shown by c of FIG. 16) from the pulse oscillator 65 is always supplied to the AND circuit 67 and simultaneously a timing pulse t1 from the timer 68 is also supplied to the AND circuit 67, which generates an output pulse (shown by d of FIG. 16). That is, the timing pulse t1 from the timer 68 previously set in accordance with the lengths of reaction times of reagents is supplied to the OR circuit 69a, the output of which is supplied to the AND circuit 67 and the control circuit of the motor 62 via the switch 66.

For this reason, an output signal from the AND circuit 67 is supplied to the pulse counter 70 and simultaneously is also supplied to the judgement AND circuit 71a.

This judgement AND circuit 71a opens its gate upon receipt of a signal from the AND circuit 67 and the timing pulse t1 from the timer 68, and then supplies its output to the operation circuit 21 of FIG. 3 for operating the reaction condition of the reagent carrier 11a.

The counter 70 counts an output pulse (shown by d of FIG. 16) generated from the AND circuit 67 while the gate thereof is opened, and the resulting count is converted into a voltage signal by the D-A converter 72 and always supplied to the comparator 64. Accordingly, this comparator 64 compares an output signal from the photoelectric detector 19 with an output signal from the D-A converter 72 and, when outputs from the D-A converter 72 are increased in number to become identical in number to outputs from the detector 19, is turned off to cease supply of its output signal to the AND circuit 67, so that the gate of the AND circuit 67 is closed and on this account the gate of the judgement AND circuit 71a is also closed. For this reason, an output being supplied to the operation circuit 21 via the AND circuit 71a is supplied to the operation circuit 21 during a period of time starting at the time at which supply of the pulse t1 from the timer 68 is effected and ending at the time at which supply of a signal from the comparator 64 is stopped. This output is subjected to operation by the operation circuit, thereby printing for indication the reaction condition of, for example, pH on a recording paper 27.

When, in this manner, measurement of the first reagent carrier 11a is completed, the test piece 11 is moved by the motor 62 so as to permit the second reagent carrier 11b to be measured. The second carrier 11b is used for test on, for example, grape sugar, and is so arranged as to be synchronized with a third timing pulse t3 from the timer 68, so that the output of the carrier 11b is supplied to the corresponding AND circuit 71c to the pulse t3, and simultaneously is subjected to the same processing as that of the carrier 11a via the first OR circuit 69a quickly to judge the reaction condition of the carrier 11b.

Similarly, a pulse t6 from the timer 68 corresponding to the carrier 11c is supplied to the corresponding AND circuit 71f, thereby to judge the reaction condition of the carrier 11c.

Where another type of test piece is used, a clinical test is carried out in accordance with the lengths of reaction times corresponding to the set lengths, i.e., t2, t3 and t4 of time different from those of the first test piece 11 only by changing-over, for example, the switch 66 to the contact C2.

Where, in still another type of test piece, items being tested are provided in a number of two, arrangement is so made that only the pulses $t5$ and $t6$ from the timer 68 are supplied to the thrid OR circuit 69c. If, in this case, for example, the pulse $t5$ is made to correspond to a test item being measured in an extremely small length of time and the pulse $t6$ to a test item being measured in a relatively large length of time, the corresponding carriers will be disposed substantially on the ends alone of the substrate 10 of the test piece and no carrier will be disposed on the intermediate portion of the substrate 10.

In this manner, a reliable and precise measurement is enabled only by selecting the contacts of the change-over switch 66 in accordance with the carrier arrangement previously made correspondingly to the lengths of reaction times of reagents. Furtheremore, if, in case arrangement of carriers is carried out, the lengths of reaction time are given in the manner of "at once", "at once", "5 sec", "10 sec" and so on in the order mentioned, carriers corresponding to "5 sec" and "10 sec" are arranged in a manner immediately following a carrier corresponding to the initial "at once", and a carrier corresponding to the remaining "at once" is arranged in a given position of the substrate having no carrier. If arrangement is made as such, no time loss will be produced to enable an extremely high precision measurement.

This invention is not limited to the device of FIG. 15, but enables a free setting of the number or arrangement condition of carriers on the test piece, the length of a timer-setting time, i.e., the number of timing pulses generated and the like, and enables the provision in various manners of the contacts of the change-over switch, OR gate circuits, AND gate circuits and the like. Further, transferring of the test piece may be effected not intermittently but continuously, and arrangement or configuration of carriers on the test piece can be variously modified.

Figure 17:
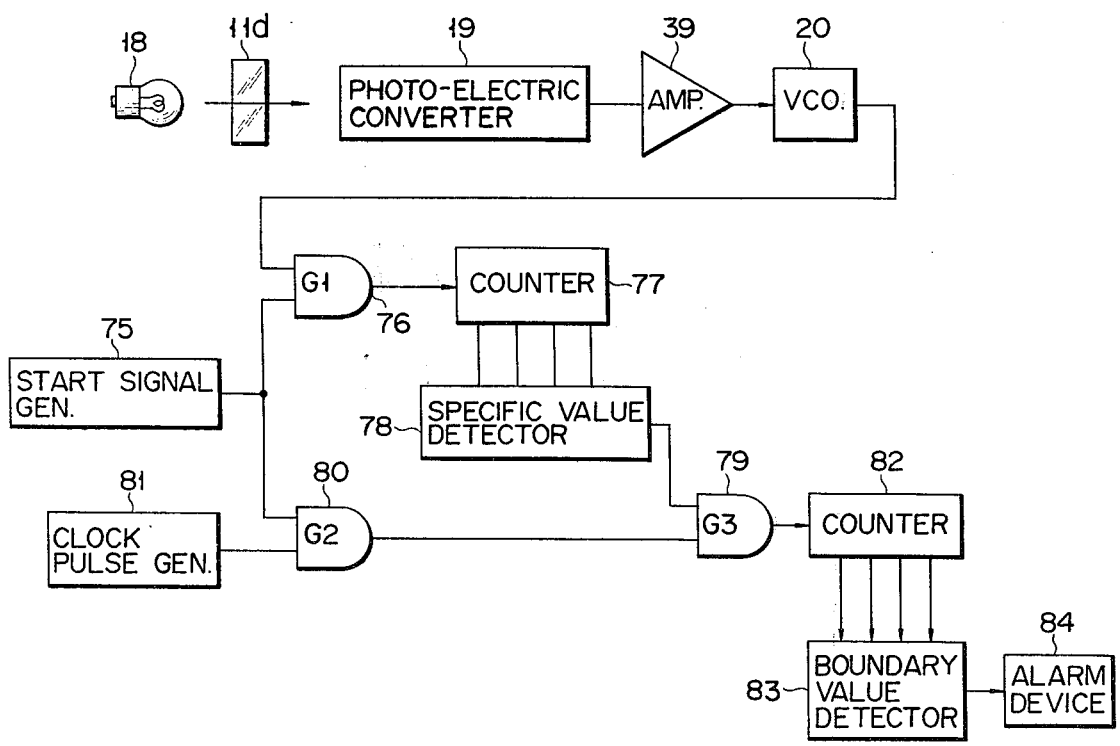
FIG. 17 is a block circuit diagram illustrating an alarm device used in association with the light source of the photoelectric detector for use in the testing system of the invention.

When, in the photoelectric detector of FIG. 2, the lamp 18 or photoelectric conversion element 19 is deteriorated, the output voltage of an electric signal from the element 19 is decreased in level to render the measurement impossible. FIG. 17 shows a device so constructed that when the output voltage level of the element 19 has been reduced to below a prescribed level, a warning or alarm is given in order to eliminate such drawback. Referring to FIG. 17, a light from the lamp 18 is reflected by the reagent carrier, for example, 11d on the chemical reaction test piece and then guided to the element 19 to be converted into an analog electric signal. After amplified by an amplifier 39, this electrical signal is supplied to a voltage-frequency converter, for example, a voltage control oscillator (VCO) 20, thereby being converted into a pulse signal having a frequency corresponding to the voltage level. This pulse signal is supplied to a counter 77 via an AND gate 76 having its gate opened by a start signal from a start signal generator 75, and is counted there. The content of the counter 77 is supplied to a specific value detector 78. The specific value detector 78 continues to supply a gate signal to an AND gate 79 to keep a gate 79 open up to detecting the specific value. The start signal also opens an AND gate 80, so that a clock pulse generated at prescribed intervals from a clock pulse generator 81 is supplied to a counter 82 after passing through the gate 79, and is counted there. When the content of the counter 77 has reached a specific value, the gate 79 is closed to stop the counting operation of the counter 82.

When, at this time, a reduction in the amount of a light from the lamp 18 or deterioration of the element 19 is caused, the output level of the element 19 is decreased to render the output pulse frequency to the VCO 20 low, so that a larger length of time is required for the content of the counter 77 to reach a specific value. When the counted value of the counter 82 is increased during said larger length of time to exceed a boundary value, an output is supplied from a boundary value detector 83 to a warning or alarm device 84 to cause an alarm to be given. Information about a reduction in the amount of a light from the lamp 18 or about deterioration of the element 19 is given by said alarm.

When the output level of the element 19 is sufficiently high, the content of the counter 77 reaches a specific value prior to the lapse of a set length of time to close the gate 79, thereby preventing the generation of an alarm signal.

Where test is made of the chemical reaction test piece by the above-mentioned device, the problem arises that an error is produced in the test result due to, for example, a drift caused by change with time in the brightness of the lamp 18 or by temperature variation in the electrical circuit section including the element 19, though not to such an extent as to require an alarm device. For the purpose of solving the foregoing problem, it is considered that a reference reflection carrier is arranged on the chemical reaction test piece in addition to the reagent carriers, and, prior to measuring the reaction degree of a test fluid, is positioned between the reagent reaction testing section, i.e., the measurement head of the photoelectric converter 19 and the photoelectric element 13, thereby causing said testing section to perform the calibration operation using the reference reflection carrier.

In this case, however, it is necessary to attach such reference reflection carrier onto each of the test pieces, which is troublesome and which causes an increase in the manufacturing cost of the device.

Figure 18:
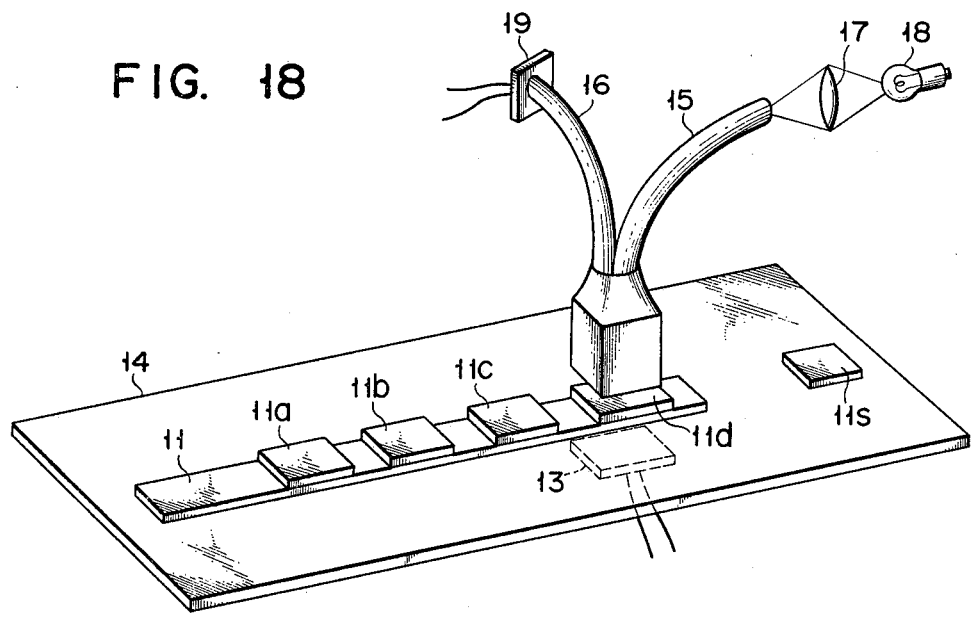
FIG. 18 is a perspective view illustrating a device adapted to calibrate the operation of the photoelectric detector using a reference reflection carrier.

FIG. 18 shows a device further improved in this respect. The device is constructed such that the table 14 for retaining the chemical reaction test piece 11 at a predetermined position is provided; a reference reflection carrier 11s having a reference reflection factor is previously mounted on the table 14; the reflection carrier 11s and the respective carriers 11a, 11b ... on the chemical reaction test piece 11 are positioned in turn between the reagent reaction testing section disposed at a prescribed position namely, the measurement head 12 of the photoelectric conversion element 19 and the photoelectric element 13 of the type detector, by moving the table 14 intermittently; and the reflection carrier 11s is positioned below said testing section prior to measuring the reaction degree of the respective test fluids of the carriers 11a, 11b ... , thereby causing the testing section to carry out the calibration operation using the reflection carrier.

The foregoing construction eliminates the necessity of providing the reference reflection carrier for each of the chemical reaction test pieces and enables the testing section as well as the test piece to have an extremely simplified construction, thereby enabling the device to be put to practical use.

There will now be described in detail the construction of the printer 26 shown in FIG. 3. A signal indicating the type of a reagent carrier on the chemical reaction test piece, namely, a signal indicating a test item is supplied to the printer 26 from the code detector 23, and simultaneously a measurement data for selecting the print character having a prescribed rank corresponding to the degree of the chemical reaction of a reagent with a test fluid from the corresponding print characters to said test item is supplied to the printer 26 from the comparator 22. Accordingly, the printer 26 is constructed such that a prescribed print item is first selected from a plurality of print items each having a plurality of print characters arranged therein in a prescribed sequential order, and the print character having a prescribed sequential position or rank is then selected from said prescribed print item, thereby effecting printing.

There will now be described an example of such printer 26 by reference to FIGS. 19 to 22.

Figure 19:
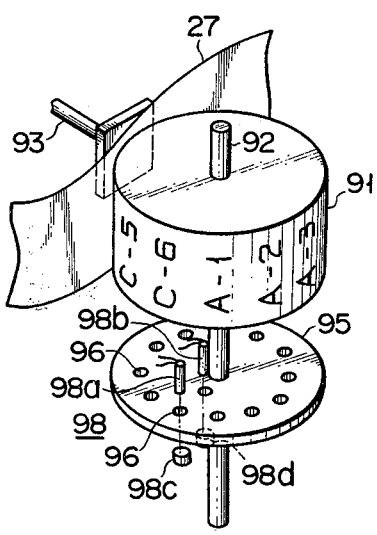
FIG. 19 is a perspective view illustrating a printing mechanism of the printer shown in FIG. 3.
Figure 20:
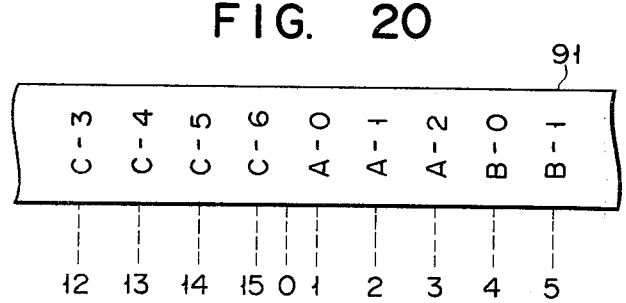
FIG. 20 is a development view of the printing plane of a printing drum illustrated in FIG. 19.
Figure 21:
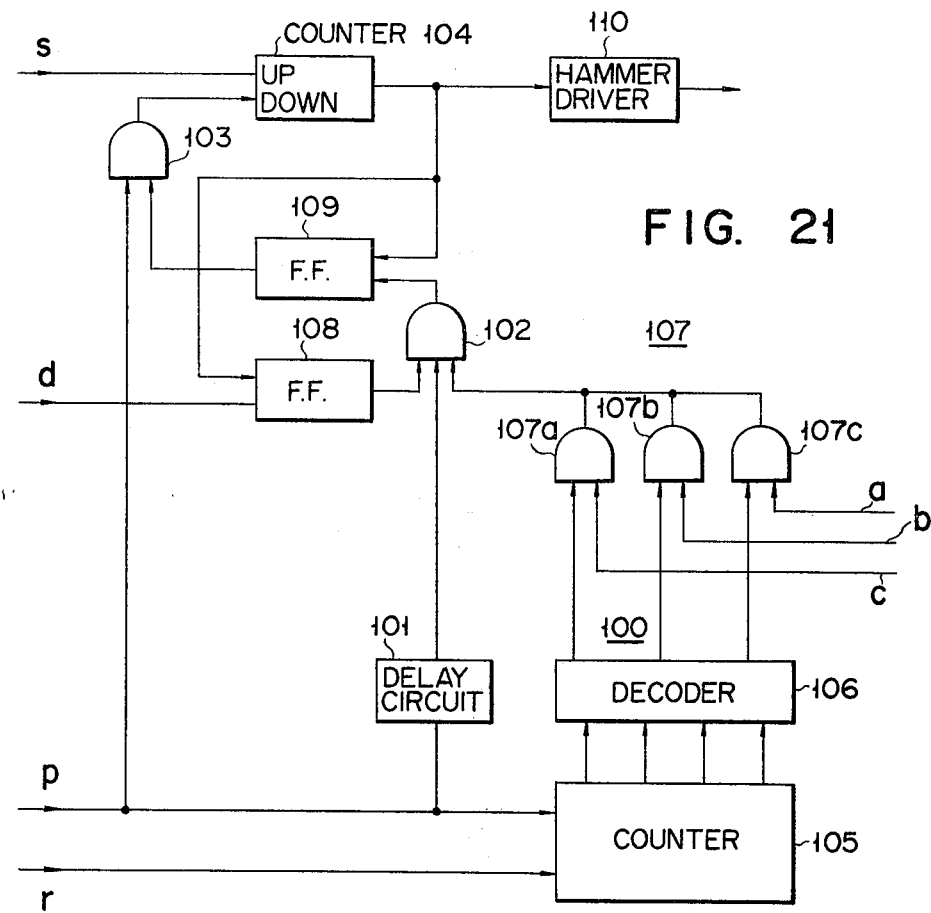
FIG. 21 is a block circuit diagram illustrating a circuit for controlling the printing mechanism of FIG. 19.

Referring to FIG. 19, a reference numeral 91 denotes a printing drum having a plurality of print characters provided on its circumference. Said printing drum 91 is fitted to a rotation shaft 92 so as to make a high speed rotation. A hammer 93 is provided for the printing drum 91 in a manner facing the circumference thereof. A printing paper 27 is inserted between the hammer 93 and the circumference of the printing drum 91. A rotation circular plate 95 is fitted to said rotation shaft 92 at a position below the printing drum 91. The rotation circular plate 95 is formed with position signal generation apertures 96 at positions of its flat surface respectively corresponding to those of said plurality of print characters provided on the circumference of the printing drum 91 and simultaneously with reset signal generation apertures 97. An aperture detection head 98 consisting of two lamps 98a and two photoelectric elements 98b is provided in a manner close to the rotation circular plate 95 so as to detect the respective apertures 96 and 97. When said print character is brought to a position at which it is to be printed by said hammer 93, the detection head 98 detects the position signal generation aperture 96 corresponding to said position of the print character to generate a later described position signal P. That is, as shown in FIG. 20, a plurality of print characters provided at equal intervals for the printing drum 91 are divided into three test items of A, B and C, and the print characters of these respective test items are arranged in the sequential order of A-0 to A-2, B-0 to B-4 and C-0 to C-6. Said position signal P is supplied to a test item judgement circuit 100 of FIG. 21, and simultaneously to a first gate circuit 102 via a delay circuit 101, and simultaneously to the down count input terminal of a reversible counter 104 via a second AND gate 103. Further, the test item judgement circuit 100 is supplied with test item designation signals a, b and c for designating said test items. The up count input terminal of said reversible counter 104 is supplied with a rank designation signal S for designating the print character of said test item bearing a specified rank. The test item judgement circuit 100 consists of a counter 105, decoder 106 and an AND gate 107. Said position signal P is counted by the counter 105, and the counted outputs are detected by the decoder 106, and said test item designation signals a, b and c are supplied to the gates 107a, 107b and 107c, respectively, of the AND gate 107. Said counter 105 makes counts in turn from the position signal corresponding to the print character A-0 to the one corresponding to the print character C-6, and is finally supplied with a reset signal r from the detection head 98 to be reset. Said decoder 106, when the counter 105 has made counts from A-0 to A-2, supplies a gate opening signal to the gate 107a, and when the counter 105 has made counts from A-0 to B-4, supplies a gate opening signal to the gate 107b, and when the counter 105 has made counts from A-0 to C-6, supplies a gate opening signal to the gate 107 c. Said AND gate 107 supplies the respective outputs of the gates 107a, 107b and 107c to said first gate circuit 102. The first gate circuit 102 is supplied with a set output from a first flip-flop 108 for making a setting operation upon receipt of a print command signal d. The first gate circuit 102 supplies its gate output to a second flip-flop 109 so as to cause it to perform a setting operation. Said second flip-flop 109 supplies its set output to said second gate circuit 103. The reversible counter 104 performs a count-up operation upon receipt of said rank designation signal S, and performs a count-down operation upon receipt of said position signal P, and when the total number of counts becomes −1, supplies a borrow signal to a hammer driver 110 to cause it to be operated and simultaneously resets the first and the second flip-flops 180 and 109. Said hammer 93 is driven by an output signal from the hammer driver 110, thereby tapping said printing drum 91 to effect printing on said printing paper 27. It is to be noted here that said rank designation signal S, when designating the minimum values of the print character rank, namely, A-0, B-0 and C-0, has a pulse number of 0 and, as the rank of a print character becomes high, increases in pulse number one by one.

With the foregoing construction, as shown in FIG. 22, the position signal P having a prescribed pulse interval which corresponds to the position of a print character is generated by rotation of the printing drum 91. This position signal P is counted in turn by the counter 105 from the print character A-0 to the print character C-6. Upon completion of counting up to the print character C-6, the counter 105 is reset by the reset signal r to start again the counting operation.

Under this condition, the print command signal d is supplied to the first flip-flop 108, thereby performing measurement of the test item A, and the rank designation signal S of this measurement result is supplied to the reversible counter 104. When the print command signal d is supplied to the first flip-flop 108 with the test item designation signal a supplied to the judgement circuit 100, the judgement circuit 100 is maintained in a condition wherein a signal for closing the gate 107c is generated from the decoder, until the position signal P being supplied to the counter 105 corresponds to the test item A, and when said position signal P has corresponded to the test item A, is brought to a condition wherein a signal is supplied from the decoder 106 to the gate 107a, resultantly to supply its output to the first gate 102. The gate 102 is already supplied with the set output of the flip-flop 108 and also supplied with the position signal P via the delay circuit 101, resultantly to supply its output to the second flip-flop 109. Since, as a result, a set signal from the flip-flop 109 is supplied to the gate 103, the position signal P corresponding to the test item A is supplied to the down-count input terminal of the reversible counter 104 via said gate 103. Accordingly, when the counter 104 carries out the count-down operation to cancel said rank designation signal S heretofore counted by the counter 104 and then further carries out the counting operation, then the counter 104 generates a borrow signal to energize the hammer driver 110. At this time, accordingly, the print character of the printing drum 91 facing the hammer 93 is printed on the printing paper 27. When, under this condition, consideration is given to the case where the rank designation signal S is supplied to the reversible counter 104, the count of the reversible counter 104 is zero and the judgement circuit 100, when the counter 105 has counted the position signal P corresponding to the print character C-6, opens the gate 103 via the gate 102 and the flip-flop 109. Since, accordingly, the reversible counter 104 is first supplied with the position signal P corresponding to the print character A-0 and, under this condition, the counter 104 generates a borrow signal to energize the hammer driver 110, the print character A-0 is printed on the printing paper 27. The same procedure applies to the other print characters. That is, the test item of the printing drum 91 is selectively determined by the test item designation signal supplied to the judgement circuit 100, and the print character of said test item having a prescribed rank is selectively determined by the rank designation signal S supplied to the reversible counter 104, whereby printing of said print character onto the printing paper is effected. It is to be noted here that said flip-flops 108 and 109 are reset by the borrow signal of the reversible counter 104.

In this manner, a simple circuit construction renders it possible automatically to select a prescribed test item from a plurality of test items having a plurality of print characters arranged in a prescribed sequential order and select a print character having a prescribed rank from those of said prescribed test item, thereby effecting printing.

The circuit construction of the test item judgement circuit is not of course limited to that described above. Further, the method of detecting the printing operation position of the hammer with respect to a print character provided for the printing drum is not of course limited to the preceding one.

Figure 23:
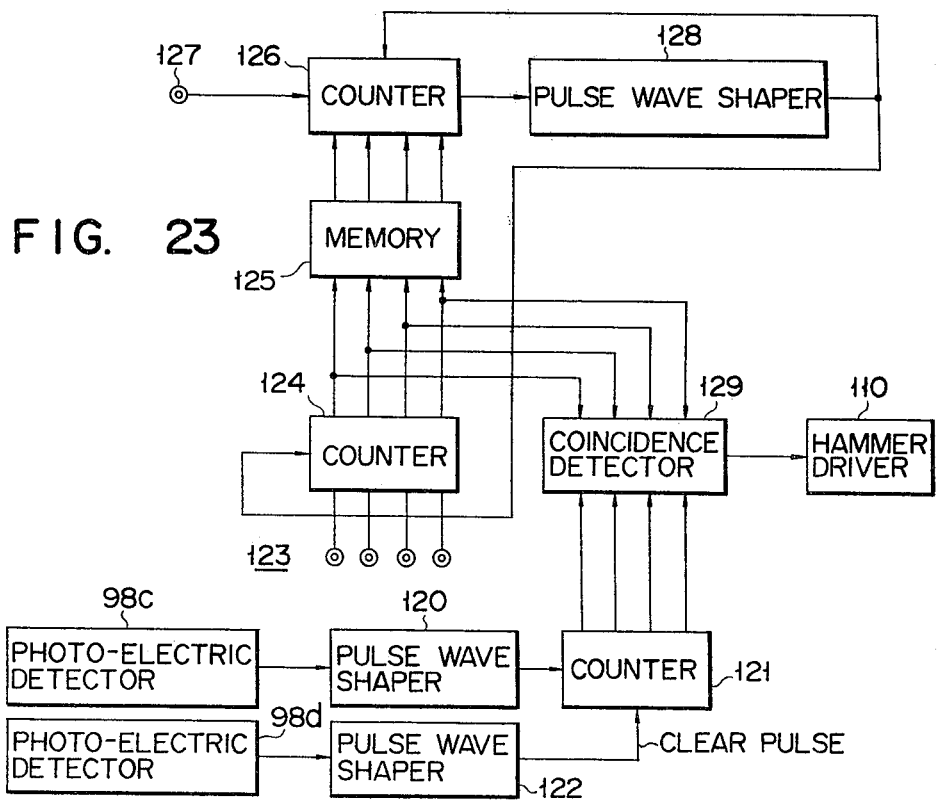
FIG. 23 is a block circuit diagram illustrating the print controlling device of another printer.

In FIG. 23, another example of the control device of the printer 26 is shown. Test results being printed are first divided into three test items A, B and C as shown in, for example, FIG. 24, and each of said three test items A, B and C is then divided into ranks 1, 2, 3 ... . The digits in each column denote the number of pulses of test data. As a printing mechanism in this case, there is used the mechanism shown in FIG. 19.

A pulse corresponding to the position of a print character provided for the printing drum 91 is obtained from the photoelectric detector 98c of FIG. 19, and after wave-shaped by a pulse wave shaper 120 of FIG. 23, is supplied to a counter 121 and counted there. The content of the counter 121 is cleared by a clear pulse similarly obtained for each rotation of the drum 91 from the photoelectric detector 98d of FIG. 19 via a pulse wave shaper. The relationship between the counts 1, 2, 3 ... 11 of the counter 121 and the respective corresponding print characters A-1, A-2 ... D-2 is as illustrated in FIG. 25.

The operation of the device shown in FIG. 23 will hereinafter be described by taking the test item B as an example. First, since the corresponding count of the counter 121 to the print character B-1 is 4 as seen from FIG. 25, a signal from a preset input terminal 123 which indicates the 4 is preset in a counter 124. The content 4 of this counter 124 designates the address 4 of a memory device 125 to cause a numerical value stored in the address 4 of the memory device 125 to be supplied to a counter 126. The numerical value read out, at this time, from the memory device 125 is a complement of the number $n1$ of pulses in the first rank of the test item B, and said number $n1$ of pulses ranges from 0 to 5 as seen from FIG. 24. Accordingly, this complement is a maximum value −5 countable by the counter 126. Next, a test pulse is supplied to an input terminal 127, and is counted by the counter 126. When the number of test pulses exceeds $n1$ (=5), counter 126 overflows to cause a carry signal from the counter 126 to be supplied to the counter 124 via a pulse wave shaper 128, so that the content of the counter 124 is increased by 1 to become 5. As the result, the content in the address 5 of the memory device 125 is set in the counter 126. This content is a complement of the number 3 of pulses, ranging from 6 to 8, in the second rank of the test item B. The counter 126 is sequentially supplied with test pulses, and if the number of these test pulses exceeds 3, a similar shift operation from the second to the third rank will be performed whereas if said number does not exceed 3, the counter 126 will not overflow, so that the division operation is completed.

Upon completion of the division operation, the content of the counter 121 is compared with that of the counter 124 by a coincidence detector 129. When the former coincides with the latter, an output from the coincidence detector 129 is supplied to the hammer driver 110 to drive the hammer 93 of FIG. 19. In this example, the content of the counter 124 is 5. Therefore, when the content of the counter 121 is 5, the hammer 93 is driven to cause a print character B-2 to be printed on the paper 27 as seen from FIG. 25.

What is claimed is:

1. A system for detecting a particular chemical component of a test fluid comprising:

a test table including thereon a chemical reaction test piece mounted thereon, said test piece having reagent carriers attached thereto, each reagent carrier containing therein a reagent for measuring the degree of chemical reaction with the test fluid;

a first photoelectric detector including means for irradiating a light onto said reagent carrier; a first photoelectric converter receiving light reflected from said reagent carrier for generating an electric signal which is a function of said light reflected from said reagent carrier; a timer having a pre-set timing period for generating measurement command signals in accordance with the respective lengths of reaction times of reagents with a test fluid; a voltage controlled oscillator coupled to said first photoelectric converter for generating pulse signals corresponding in number to outputs from said first photoelectric converter; and a gate circuit coupled to said timer and to said voltage controlled oscillator for supplying output pulse signals corresponding in number to said measurement command signals;

means for intermittently moving one of said photoelectric detector and said test table relative to the other;

type data detection means for detecting a type data indicating the type of the chemical reaction test piece mounted on the test table, which includes a second photoelectric converter for scanning a chemical reaction test piece having reagent carriers attached onto one end side of its elongate light-permeable substrate and a light-impermeable pad attached onto the other end side and permitting the type of said reagent carriers to be coded by the number of the reagent carriers and a distance between said pad and a reagent carrier adjacent the same; means for generating a coded type data from the output of said second photoelectric converter; temporary memory means for temporarily storing therein said generated coded type data; and means for reading out the individual type data from said temporary memory means;

an operation circuit coupled to the output of said gate circuit and to said reading out means for deriving a test from said type data read out from said temporary memory means;

a memory having comparison data pre-stored therein, said comparison data indicating the respective ranks of a plurality of test items;

means coupled to said memory and to said operation circuit for comparing the stored comparison data with the test data; and printing means for printing the test data on a recording paper as a function of the output of said comparison means and the output of said type data detection means.

2. A system according to claim 1 wherein a reference reflection carrier is provided on said test table; and a reference data corresponding to a light reflected from said reference reflection carrier is detected in advance of the reagent carrier by said first photoelectric detector, thereby calibrating said test data by said reference data.

3. A system according to claim 1 wherein said first photoelectric detector includes a first counter for counting output pulses from said voltage control oscillator; a specific value detector coupled to said first counter for generating an output only until the count of said first counter reaches a specific value; a source of clock pulses; a second counter coupled to said clock pulse source and to said specific value detector for counting clock pulses during the period of time in which outputs are generated from said specific value detector; a boundary value detector for generating an output when the count of said second counter exceeds a predetermined boundary value; and an alarm signal generation device driven by the output of said boundary value detector.

4. A system according to claim 1 wherein said first photoelectric detector includes a light transmitting and receiving means; first and second light guides connected at one end to the light transmitting and receiving means; a lamp for irradiating light from the other end of said first light guide onto said reagent carrier through said first light guide and a light transmitting and receiving means; a first photoelectric conversion element connected to the other end of said second light guide for receiving light reflected from said reagent carrier through the second light guide; a second photoelectric conversion element for receiving light transmitted through the chemical reaction test piece and arranged in a manner facing said light transmitting and receiving means at a prescribed spacing in which said chemical reaction test piece is to be inserted.

5. A system according to claim 1 wherein said means for intermittently moving includes a stepped cam rotating at a given speed and a device coupled too said stepped cam for reciprocatingly moving said test table in accordance with the rotation of said stepped cam; and said type data detection means includes a position signal detector including position indication apertures formed in said stepped cam at pitches each corresponding to the amount of movement of said table, said second photoelectric converter detecting said position indication aperture, and means for forming a position signal corresponding to a logical product of the output of said first photoelectric converter and that of said second photoelectric converter.

6. A system according to claim 5 wherein said coded type data generating means include a first amplifier coupled to said position signal forming means for amplifying said position signal; a first Schmitt circuit responsive to the amplified position signal for generating a first pulse signal corresponding to a prescribed level of said position signal; a one-shot circuit for generating a one-shot pulse signal in response to the output of said Schmitt circuit; a counter for counting the output pulses of said Schmitt circuit; a decoder coupled to said counter for generating step-advancement signals in accordance with the contents of said counter; a plurality of differential circuits for differentiating each of said step-advancement signals; a second amplifier coupled to said first photoelectric converter for amplifying said electric signal generated thereby; a second Schmitt circuit responsive to the amplified electric signal for generating a second pulse signal corresponding to the amplified electric signal; a plurality of AND gates having respective first inputs coupled to respective ones of said differential circuits and respective second inputs coupled in common to said second Schmitt circuit; a plurality of flip-flops respectively coupled to said AND gates for temporarily storing the outputs of said AND gates; and a judgement-logical gate circuit coupled to the outputs of said flip-flops for producing type judgement signals corresponding to the test pieces.

7. A system according to claim 3 which further comprises a judgement-logical product gate circuit including AND gates and OR gates for producing type distinguishing signals representing said reagent carriers responsive to said type judgment signals produced by said judgment-logic gate circuit and to said step-advancement signals generated by said decoder.

8. A system according to claim 1 wherein said printing means includes a rotatable printing drum having its side circumference divided into a plurality of sections and having a plurality of print characters belonging to the same print item provided for each section with the respective ranks of said print characters determined; a printing hammer provided facing said rotatable printing drum; a driver for driving said hammer; means for obtaining a print item designation signal from said type data generated by said type data detection means; means for obtaining a rank designation signal for designating a print character in the print item having a prescribed rank; a reversible counter having one input terminal supplied with said rank designation signal; means for obtaining the rank signals of print characters from said printing drum; means for selecting from said rank signals position signals corresponding to a print item designated by said rank signals and for supplying said position signals to the other input terminal of said reversible counter; means for generating, when said position signals have been counted by the reversible counter by the number of said rank designation signals supplied thereto, a borrow signal from said reversible counter; and means coupled to said borrow signal generating means for driving by said borrow signal.

9. A system according to claim 1 wherein said printing means includes means for converting the output of said first photoelectric detector into a measurement pulse signal; a first counter for counting the measurement pulse signals; a memory device coupled to said counter for storing the rank width of the measurement value of said measurement pulse signals which is indicated by the number of pulses; a second counter for generating a signal for designating an address in said memory device; a character printing drum; a third counter coupled to said printing drum for detecting the type of a character provided on said printing drum; and a comparator for comparing the contents of the second counter with that of the third counter.

* * * * *

UNITED STATES PATENT AND TRADEMARK OFFICE
CERTIFICATE OF CORRECTION

PATENT NO. : 3,932,133
DATED : January 13, 1976
INVENTOR(S) : Hiroshi ISHIKAWA

It is certified that error appears in the above-identified patent and that said Letters Patent are hereby corrected as shown below:

In the heading of the patent, change inventor's address from "Fussa, Japan" to --Tokyo, Japan--;

In the heading of the patent, add the following Japanese application to the priority data:

--June 20, 1974   Japan................49-70688--;

Column 15, line 65, after "device coupled" change "too" to --to--.

Signed and Sealed this twenty-seventh Day of April 1976

[SEAL]

Attest:

RUTH C. MASON
Attesting Officer

C. MARSHALL DANN
Commissioner of Patents and Trademarks